US006200330B1

(12) United States Patent
Benderev et al.

(10) Patent No.: US 6,200,330 B1
(45) Date of Patent: Mar. 13, 2001

(54) SYSTEMS FOR SECURING SUTURES, GRAFTS AND SOFT TISSUE TO BONE AND PERIOSTEUM

(76) Inventors: Theodore V. Benderev, 26975 Magnolia Ct.; Timothy Charles Ryan, 25082 Sausalito St., both of Laguna Hills, CA (US) 92653

( * ) Notice: Subject to any disclaimer, the term of this patent is extended or adjusted under 35 U.S.C. 154(b) by 0 days.

(21) Appl. No.: 09/197,938

(22) Filed: Nov. 23, 1998

(51) Int. Cl.$^7$ .................................................. A61B 17/04
(52) U.S. Cl. ........................ 606/232; 606/75; 411/358; 411/359; 411/446
(58) Field of Search ...................... 606/72, 73, 75, 606/219, 221, 232, 222, 223, 224, 225; 411/485, 446, 447, 448, 449, 471, 472, 480, 356–359

(56) References Cited

U.S. PATENT DOCUMENTS

| | | | |
|---|---|---|---|
| 2,865,376 | * 12/1958 | Pellier et al. | 606/226 |
| 4,738,255 | 4/1988 | Goble et al. . | |
| 4,932,962 | * 6/1990 | Yoon et al. | 606/224 |
| 5,242,457 | * 9/1993 | Akopov et al. | 606/144 |
| 5,370,662 | 12/1994 | Stone et al. | 606/232 |
| 5,443,482 | 8/1995 | Stone et al. | 606/232 |
| 5,501,683 | * 3/1996 | Trott | 606/72 |
| 5,611,515 | 3/1997 | Benderev et al. | 128/898 |
| 5,620,012 | 4/1997 | Benderev et al. | 128/898 |
| 5,749,884 | 5/1998 | Benderev et al. | 606/167 |
| 5,766,221 | 6/1998 | Benderev et al. | 606/232 |
| 5,836,314 | 11/1998 | Benderev et al. | 128/898 |
| 5,842,478 | 12/1998 | Benderev et al. | 128/898 |

OTHER PUBLICATIONS

One–page brochure, *How Will the Vesica® Procedure Restore Control?*, Boston Scientific/Microvasive®, Apr. 1998.

\* cited by examiner

*Primary Examiner*—Michael Buiz
*Assistant Examiner*—David O. Reip
(74) *Attorney, Agent, or Firm*—Stetina Brunda Garred & Brucker

(57) ABSTRACT

Devices for affixing sutures, grafts and tissues to bone, and soft tissue such as periosteum. In a first embodiment, the invention comprises a piton member implantable within bone having a post or eyelet formed thereon to which the suture or tissue may be attached. The piton member is designed to become more firmly secured within the bone when pressure is applied to a first axis pushing the piton member into the bone, but may be easily removed when such force is applied in a generally opposed direction. In a second embodiment, the invention comprises affixation devices that are designed to detachably ensnare with periosteum. Such devices are provided with attachment structures, such as one post, eyelet or other means for securing sutures, grafts, synthetic materials or tissues.

2 Claims, 4 Drawing Sheets

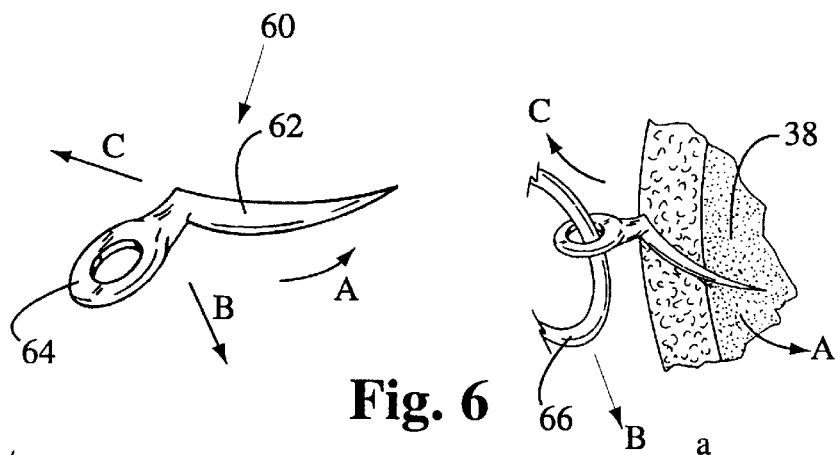
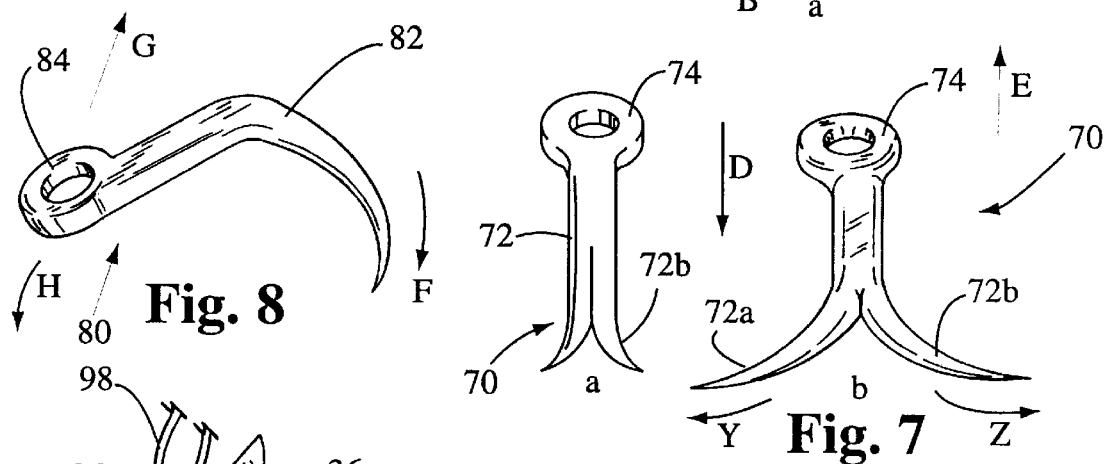
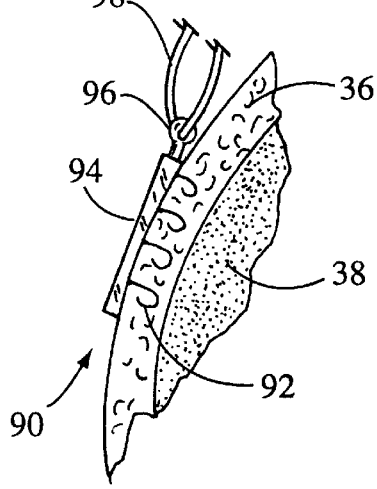
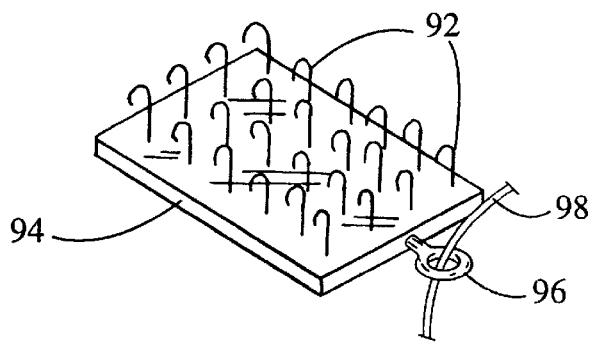
Fig. 6
Fig. 7
Fig. 8
Fig. 9
Fig. 10

SYSTEMS FOR SECURING SUTURES, GRAFTS AND SOFT TISSUE TO BONE AND PERIOSTEUM

FIELD OF THE INVENTION

The present invention relates generally to surgical affixation devices, and more particularly devices for affixing sutures, grafts, soft tissue, synthetic materials, and the like to bone, periosteum, ligaments, fascia and other soft tissue.

BACKGROUND OF THE INVENTION

The use of surgical suture anchors for use in attaching soft tissue to bone is well known in the art. In this regard, such anchoring mechanisms have found widespread applicability for a number of surgical procedures, and in particular orthopedic, gynecologic and urologic procedures. Exemplary of such devices include bone screws or anchors that are implantable within bone which further have formed thereon an eyelet or other type of assembly to which may be affixed suture lines or a segment of soft tissue. Exemplary of such devices include those devices disclosed in U.S. Pat. Nos. 5,370,662 and 5,443,482 to Stone, et al. and U.S. Pat. No. 4,738,255 to Gobel, et al.

Generally, prior art anchor systems take one of two forms. The first configuration typically comprises a self-tapping bone screw, typically made of titanium, having an eyelet formed thereon to which the sutures or other material may be attached. In the alternative prior art configuration, the device comprises an anchor member, which may take the form of an arrowhead or similar conical configuration, which further includes a shaft or attachment member extending therefrom, the latter being formed to have one or more apertures to which the sutures or other material may be attached.

With respect to the surgical installation of such devices, bone-screw mechanisms must necessarily be screwed in position, typically by a battery-powered screw driver, at a target site upon a particular bone. Anchor devices of the other aforementioned variety typically must be "shot" into position at a particular site within a bone, typically via a spring-loaded delivery mechanism. Exemplary of such bone-anchor insertion devices include the In-Fast and In-Tac bone screw and bone anchor fixation devices produced by Influence, Inc. of San Francisco, Calif.

Although such prior art anchor devices generally provide sufficient support to the various sutures and grafts affixed thereto, such fixation devices suffer from numerous drawbacks. In this regard, it is difficult for the surgeon to accurately deploy the insertion device such that the anchor is correctly inserted at the target site. Moreover, substantial difficulty arises in removing such devices. This latter task is especially problematic with respect to bone-screw devices insofar as the surgeon attempting to remove the same must take great care to insure that the removal device, also typically comprising a battery-powered screw driver, properly unscrews the anchor member from its seated position. Other prior art anchor devices are even further problematic insofar as the same are often irretrievable once deployed, especially in situations where the same are deployed too deeply into the bone mass.

Additional problems exist with prior art bone fixation systems insofar as the same have a tendency to become dislodged over time from their seated position. In this regard, due to the repetitive application of stress or strain upon the bone anchor via the suture or soft tissue attached thereto, such anchors can eventually become loose and slip out of engagement from their fixed position. This tendency is especially likely to the extent repetitive and persistent application of strain and stress is applied in one specific direction or orientation. Moreover, even to the extent such bone anchoring systems remain securely in position, recent research tends to indicate that such bone fixation devices have a tendency to actually cut the sutures sought to be held thereby.

Separate and apart from the drawbacks associated with the use of prior art bone anchoring systems is the fact that often times anchor systems provide far more structural support than is necessary for a given surgical application. In this respect, numerous surgical procedures requiring the fixation of sutures and/or soft tissue require only a minimal degree of tension. Exemplary of, and perhaps most well-known of such procedures include transvaginal sling surgery to treat incontinence, which essentially involves the formation of a graft positioned beneath the urethra with the opposed ends thereof being secured to either one of the abdominal fascia, Cooper's ligament or pubic bone. While such slings typically require little to no tension once fixed into position, due to the lack of alternative means for affixing the opposed ends of such sling into position relative to the pubic bone, such prior art bone anchor devices must necessarily be deployed. As a result, operative time is increased and the patient undergoing such procedures is subjected to a far more traumatic experience and has a possibly greater susceptibility of becoming infected by virtue of the deployment of such anchor devices than would otherwise occur to the extent alternative, less traumatic affixation devices could be deployed.

Accordingly, there is a need in the art for systems and devices for affixing sutures, grafts, soft tissues, synthetic materials, and the like to bone that are easier to deploy, remove and can remain more firmly seated into position than prior art devices. There is additionally a need for such devices that can be utilized in a wide variety of surgical applications and may be further customized for use for particular applications such that an optimal degree of support or leverage can be provided thereby. There is further a need in the art for affixation systems and devices that can provide for a less traumatic means for affixing sutures, grafts, soft tissues, synthetic materials, and the like into position that are less traumatic, easier to deploy, and may be readily removed and repositioned at a particular site than prior art systems and devices.

SUMMARY OF THE INVENTION

The present invention specifically addresses and alleviates the above-identified deficiencies in the art. In this regard, the present invention is directed to novel devices for the attachment of sutures, grafts and other types of tissues and materials to bone, periosteum, ligaments, fascia and other soft tissue as may be warranted in a given surgical procedure. The devices of the present invention are particularly well suited for the attachment of one or both of the opposed ends of a suburethral sling for use in suburethral sling surgery, but are by no means limited to such particular application.

In a first preferred embodiment, the invention comprises an implant implantable within bone, ligaments, fascia and other soft tissue at a desired location. The implant comprises a piton portion designed to pierce into and engage with the bone, or tissue, and a support structure coupled therewith, the latter of which may take the form of a post, hook or eyelet to which the suture, graft, or tissue may be attached.

The piton portion of the implant is specifically designed to become more firmly embedded within the bone or other tissue when pressure is applied to the support structure in a first direction, but may be dislodged or removed when the implant is pulled in an opposed or second direction. The piton member may be further selectively sized and adapted for use in a particular application, and may be particularly designed to penetrate up to certain depths and/or be capable of supporting a specific quantity of mass or weight. The implants of the present invention may further include a handle member formed thereon to facilitate the insertion and removal of the implant from its fixed or seated position within the bone/tissue.

In a second preferred embodiment, the invention comprises an affixation device designed to secure sutures, grafts, tissues, synthetic materials, and the like to periosteum (i.e., the thick fibrous membrane covering the surface of bones) and other soft tissue. According to a preferred embodiment, the affixation device includes a backing or base member having at least one, and preferably a multiplicity of hook members that are sized and adapted to hook into and ensnare with the periosteum or tissue. The hook members may be specifically designed to become partially embedded within the periosteum tissue, to thus provide relatively loose connection that is easier to remove, and may be designed to penetrate deeper within the periosteum tissue to thus provide a more secure method of attachment. An attachment member formed upon the base member is further provided to which may be attached a suture or a portion of a graft. In an alternative preferred embodiment, the invention comprises an implantable tack consisting of a hub member having at least one, and preferably two or more hook members formed thereon, the latter being designed to extend through the graft or tissue and become ensnared with and embedded in the periosteum such that the graft or tissue becomes interposed between and affixed into position relative the tack and periosteum. The affixation devices according to such embodiments are specifically designed for selective attachment and detachment, and are further designed to provide more atraumatic means for the attachment of the suture or graft to a target location via the periosteum and soft tissue. Such a fixation devices, however, may be adapted such that the same are designed to pierce into and become embedded within the bone, as per the other aforementioned embodiments.

In yet another embodiment of the present invention, there is provided a novel surgical staple that is also designed to secure a graft or other types of tissues and materials to the bone, periosteum, or other soft tissue at a specific site or location. The staples of the present invention are preferably formed from plastically deformable materials having opposed ends that are designed to is penetrate through the graft/tissue and hook into the bone, periosteum or soft tissue at a selected site of fixation. Once secured in position, the staples are operative to assume an expanded configuration such that the hooks formed thereby become more firmly embedded within the bone/tissue at the target site of fixation to thus further secure attachment of the graft thereto. Preferably, such staples may be fabricated from a shape-memory material, such as nitinol, which thus enables the staple to assume the compressed configuration when at room temperature, but transition to the operative, expanded configuration when warmed to body temperature, as will occur when the device is deployed. Such materials further enable the staples of the present invention to be removed, as may be necessary, during a given procedure or later procedures. Conversely, such staples may be formed material that enable the same to compress or contract once secured into position to thus provide for a more secure means of attachment.

The present invention further comprises novel surgical approaches for the affixation of a transvaginal sling during transvaginal sling surgery. More particularly, such surgical procedure involves securing such sling into position, namely, beneath the urethra, with the opposed ends thereof being secured to the posterior portion of the pubic bone in the retropubic space. The opposed ends of the sling may be attached to either the periosteum of the pubic bone or to the pubic bone itself using the novel affixation devices of the present invention. Advantageously, such surgical procedure eliminates the needs to form a abdominal incision, which typically must be made utilizing conventional surgical procedures. The novel affixation method of the present invention during such surgery further provides for the ingrowth of the opposed ends of the graft to a target site on the pubic bone or the periosteum thereof that eliminates any intervening abdominal fascia that would otherwise become interposed between the anchor and opposed ends of the sling sought to be secured into position.

It is therefore an option of the present invention to provide surgical implantation devices to facilitate the attachment of sutures, grafts, tissues and the like to bone, periosteum and soft tissue that are easier to implant and remove than prior art devices, and are further capable of providing greater support or leverage to the structures coupled therewith than prior art devices.

Another object of the present invention is to provide surgical implantation devices for the attachment of sutures, grafts, tissues and the like to bone, periosteum and soft tissue that can be utilized in a wide variety of surgical procedures, and in particular suburethral sling surgery, and that may be further designed to provide an optimal degree of support for a given quantity of mass or weight as may be necessary for a given surgical procedure.

Another object of the present invention is to provide devices for the affixation of sutures, grafts, tissues and the like to periosteum and soft tissue at a specific site or location that does not require any anchoring mechanism to be inserted into the bone.

Another object of the present invention is to provide devices for the attachment of sutures, grafts, tissues and the like to bone, periosteum and soft tissue at a specific location that are less traumatic than other prior art affixation devices.

Another object of the present invention is to provide devices for the attachment of sutures, grafts, tissues and the like to bone, periosteum and soft tissue at a specific location that are easily attachable to and detachable from a point of fixation than prior art devices and re-attachable as may be necessary for a given procedure or future procedures.

Still further objects of the invention include methods and devices for securing sutures, grafts, tissues and the like to bone, periosteum and soft tissue that are of simple construction, may be easily and readily utilized for a variety of surgical procedures, may be readily adapted for use in a wide variety of surgical procedures, and provide an equal, if not greater degree of support or leverage than prior art devices. It is additionally an object of the present invention to provide a novel surgical procedure for the formation and affixation of a suburethral sling whereby the opposed ends of the sling are secured to the posterior side of the pubic bone in the retropubic space with the opposed ends of the sling being secured to either the periosteum, Cooper's ligament, fascia or the pubic bone itself.

BRIEF DESCRIPTION OF THE DRAWINGS

These, as well as other features of the present invention will become more apparent upon reference to the drawings wherein:

FIGS. 5(a) and (b) are perspective views of prior art anchor devices.

FIGS. 6 and 6(a) are a perspective view of a surgical implant constructed in accordance with a preferred embodiment of the present invention for use in attaching sutures, grafts, tissues and the like to bone, periosteum, and soft tissue, and a side view of the same being inserted into bone.

FIG. 7(a) is a perspective view of a surgical implant constructed in accordance with a second preferred embodiment of the present invention for use in attaching sutures, grafts, tissues and the like to bone, periosteum, and soft tissue. Such figure depicts the surgical implant assuming a pre-insertion configuration.

FIG. 7(b) is a perspective view of the surgical implant of FIG. 7(a) with the implant assuming an expanded, anchoring configuration.

FIG. 8 is a perspective view of a surgical implant constructed in accordance with a third preferred embodiment of the present invention for use in attaching sutures, grafts, tissues and the like to bone, periosteum, and soft tissue.

FIG. 9 is a cross-sectional view of the pubic bone and periosteum thereof having an affixation device affixed with the latter, said affixation device being constructed in accordance with a fourth preferred embodiment of the present invention useful for securing sutures, grafts, tissues and the like to bone, periosteum and soft tissue.

FIG. 10 is a perspective view of the affixation device depicted in FIG. 9.

DETAILED DESCRIPTION OF THE PREFERRED EMBODIMENTS

Figure 1:
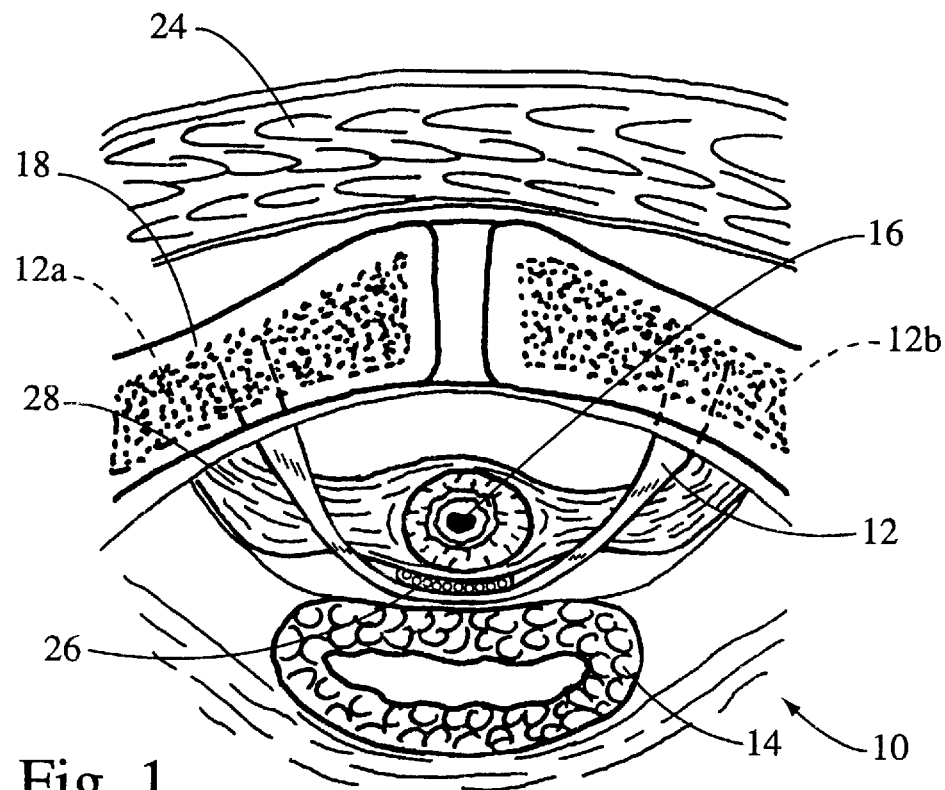
FIG. 1 is a frontal, cross-sectional view of the rectus fascia, pubic bone, urethra and vagina further depicting a sling member positioned about the urethra or in which the respective ones of opposed ends of the sling are secured to the pubic bone.

The detailed description as set forth below in connection with the appended drawings is intended as a description of the presently preferred embodiments of the invention, and is not intended to represent the only form in which the present invention may be constructed or utilized. The description sets forth the functions and sequences of steps for constructing and operating the invention in connection with the illustrated embodiments. It is understood, however, that the same or equivalent functions and sequences may be accomplished by different embodiments and that they are also intended to be encompassed within the scope of this invention.

Referring now to the drawings, and particularly FIGS. 6–15, there are shown various embodiments of the devices and systems of the present invention for securing sutures, grafts, tissues and synthetic materials, and the like to bone, periosteum and soft tissue. As is well known in the practice of medicine, a wide variety of surgical procedures often necessitate the use of anchoring devices for purposes of attaching suture lines and grafts to bone. Exemplary of such anchoring devices include those disclosed in U.S. Pat. Nos. 5,370,662 and 5,443,482, the teachings of which are expressly incorporated herein by reference as frequently deployed in orthopedic, gynecologic, and urologic surgical procedures.

Figure 2:
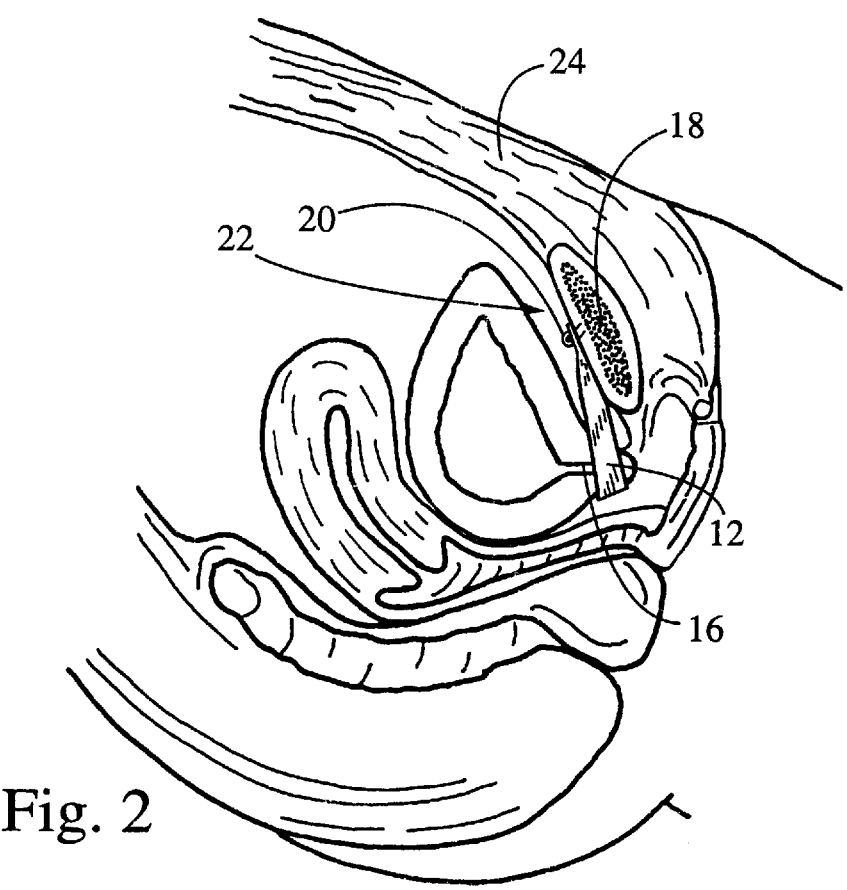
FIG. 2 is a side cross-sectional view of the anatomical structures depicted in FIG. 1 and further depicting the fastening arrangement by which the sling is anchored to the posterior portion of the pubic bone.

Among the more well-known surgical procedures incorporating the use of such anchoring devices include transvaginal sling surgery. As illustrated in FIGS. 1 and 2, such surgical procedure 10 involves the formation of a sling 12, which may comprise a harvested graft from a donor, or the patient's own tissue or an elongate strip of fabricated synthetic material, that is introduced via an incision made to the vaginal wall 14 and selectively positioned beneath the urethra 16. Once properly positioned, the sling 12 is secured into position. Unlike conventional transvaginal sling surgery, however, the sling 12 as depicted in FIGS. 1 and 2 is secured and tied into the posterior side of the pubic bone 18, via an anchoring mechanism 20, more clearly depicted in FIG. 2. As will be appreciated by those skilled in the art, the method by which the opposed ends 12a, 12b of the sling 12 are secured, namely to the posterior side of the pubic bone 18, represents a novel approach insofar as such sling 12 is stitched into position in the retropubic space 22, as opposed to the suprapubic space which is conventionally utilized. Unlike alternative methods of performing suburethral sling procedures, such transvaginal sling surgical procedure advantageously dispenses with the need to form an incision in the patient's lower abdomen 24 to thus enable the surgeon to gain access to the various anatomical structures, such as the abdominal fascia, pubic bone, or Cooper's ligament, to which the opposed ends of such sling are to be attached. As is well known, performing such abdominal incision increases operative time, increases the chances of infection, delays recovery time, and leaves undesirable scarring. Moreover, such sling procedure as depicted does not require that the sutures or opposed ends of the grafts be caused to penetrate through the intervening pubocervical fascia 28, depicted in FIG. 1, present in the retropubic space 22 which, as will be appreciated by those skilled in the art, prevents ingrowth of the opposed ends 12a, 12b of the sling sought to be secured in position.

As a result of the support imparted by the sling 12 to the urethra 16 during such times as the patient makes provocative gestures, as occurs during coughing, such sling 12 serves as a support that prevents incontinence occurring during such provocative event. To insure that the sling 12 is positioned such that the same imparts an optimal degree of support to the urethra 16, it is contemplated that a tension/pressure monitor 26, as depicted in FIG. 1, may be utilized during the performance of such surgical procedure. Such tension/pressure monitors 26 may take any of a variety of forms such as those disclosed in Applicant's co-pending U.S. Pat. application Ser. No. 09/157,466, the teachings of which are expressly incorporated herein by reference.

Figure 3:
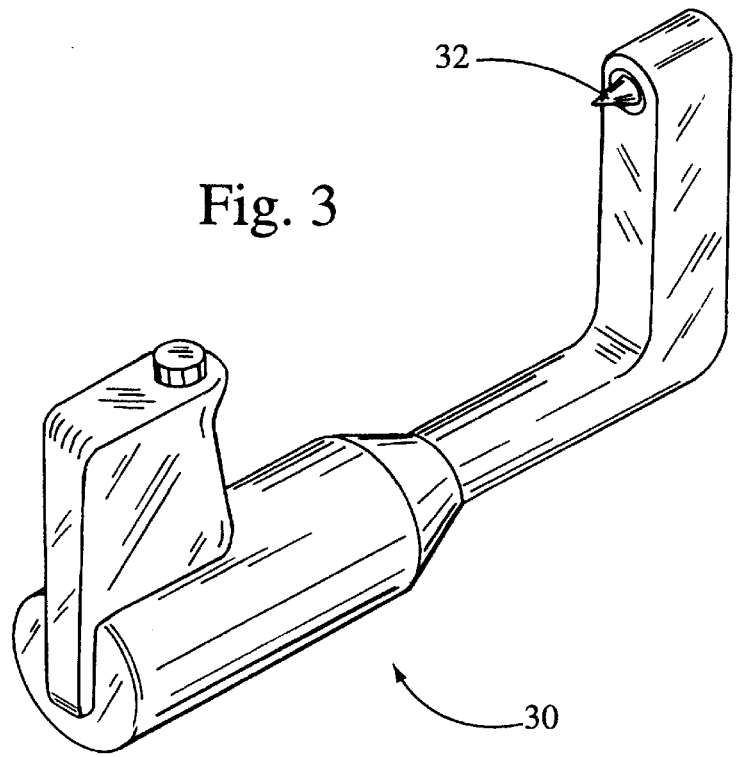
FIG. 3 is a prior art surgical instrument utilized to secure the anchor member depicted in FIG. 2 to the posterior of the pubic bone.

In order to provide an anchoring mechanism necessary to secure the sling into position during transvaginal sling procedures, however, there must be deployed the aforementioned anchoring device 20. As depicted in FIG. 3, there is shown one such anchor deployment device 30, also known in the practice of medicine as a bone screw inserter, which allows for bone-screw fixation. Perhaps the most well-known of such devices include the In-Fast and In-Tac bone screw and bone anchor fixation devices produced by Influence, Inc. of San Francisco, Calif. Such affixation devices are formed to have a generally "U" shape as shown that enables the distal-most end 32 thereof to be easily inserted into the vagina and be correctly positioned on the posterior portion of the pubic bone. As will be appreciated by those skilled in the art, the distal-most end 32 of such fixation deployment devices 30 are designed to deploy an anchoring device by screwing or embedding the same into bone at a specific site.

Figures 4, 5:
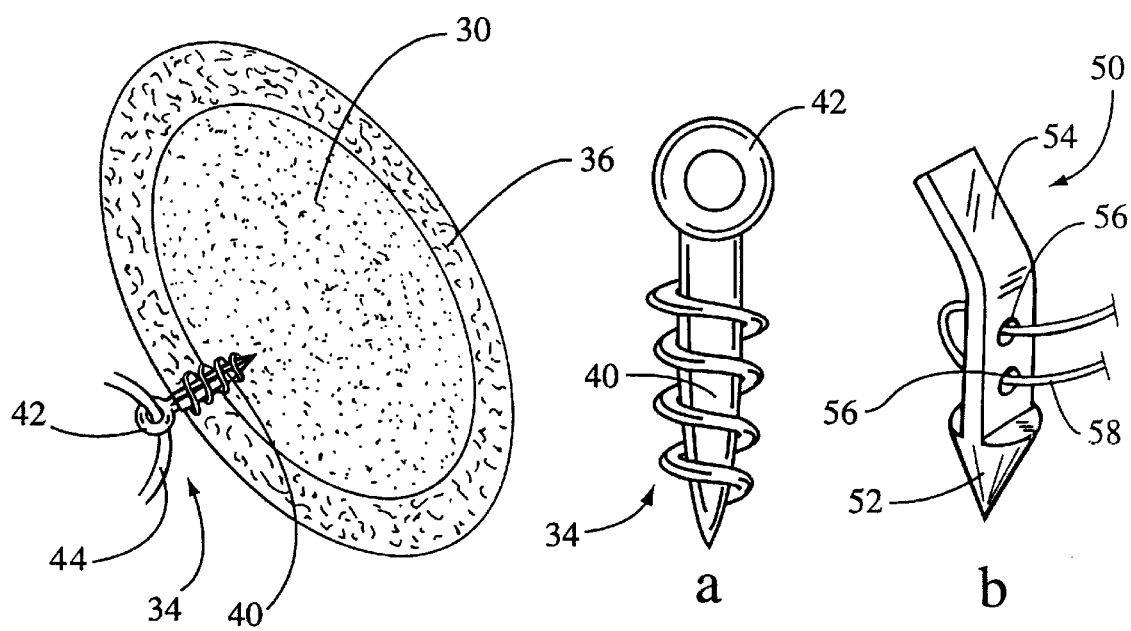
FIG. 4 is cross-sectional view of the pubic bone having a prior art anchor device secured thereto.

As more clearly seen in FIG. 4, once deployed, the anchor devices 34 are advanced through the periosteum 36 and become embedded into the bone. To provide means for affixing the suture lines or grafts thereto, there is typically formed on the anchor devices a post, hook or eyelet, as shown. Among the more well-known designs of such anchoring devices currently in use include those depicted in FIGS. 5(a) and (b). The first such prior art device 34 depicted in FIG. 5(a) comprises a self-tapping bone screw 40, typically made of titanium, having an eyelet 42 formed thereon to which the sutures 44 or other material may be attached, as shown in FIG. 4. In the alternative prior art configuration 50 depicted in FIG. 5(b), the anchor fixation device comprises an anchor portion 52, which may take the form of a conical member having a shaft or attachment member 54 extending therefrom, the latter being formed to have one or more apertures 56 thereon to which sutures 58 or other material may be attached. Such devices are typically "shot" into position via spring-loaded insertion devices, such as the In-Tac device discussed above.

Although such prior art anchor devices, such as those depicted in FIGS. 5(a) and (b), generally provide sufficient support to the various sutures and grafts affixed thereto, such fixation devices 34, 50 suffer from numerous drawbacks. With respect to the bone-screw fixation devices 34, such devices are difficult to deploy and fix into position. In this regard, such screw fixation devices 34 require the battery-operated inserters 30 depicted in FIG. 3 that must necessarily drill the fixation device 34 into position. Removing such devices 34 is further problematic insofar as the same must necessarily be unscrewed from their position, which as those skilled in the art will appreciate requires meticulous precision.

Anchor devices 50 are also problematic insofar as the same are not only difficult to deploy, typically via a spring-loaded gun mechanism, but are often times irretrievable once deployed. In this regard, once such fixation device 50 is sufficiently embedded within the bone, the anchor portion 52 thereof cannot be reversibly extracted from its embedded position within the bone. As such, to the extent such anchoring devices 50 have been inappropriately deployed (e.g., deployed at a wrong location), there is little, if any, recourse to retrieve the same. Additionally, such prior art bone screws 34 and anchors 50 have the ability to become loosened and dislodged from their position once a sufficient amount of pressure is applied thereto over time. The probability of becoming dislodged is further increased in those situations where a persistent strain is applied to such devices in a single direction, as can occur when a suture or graft is hung upon the anchoring device. In such circumstances, surgical intervention is necessary to not only retrieve the dislodged screw or anchor, but also deploy yet another of such devices as per the original surgical procedure.

Referring now to FIGS. 6–8, there are shown three embodiments 60, 70, 80 of a surgical implant insertable into bone (as well as periosteum, ligaments, and other soft tissue) which are useful in providing means to secure sutures, grafts, tissues, synthetic materials, and the like to bone, as may be necessary for a given surgical procedure. Each of the embodiments depicted have the advantage of being easy to insert and remove, as well as provide an equal, if not greater, degree of support than prior art devices. Such novel implants further have the ability to remain more firmly seated into position once embedded in bone than such prior art devices.

Referring now to FIG. 6, there is shown a first embodiment 60 of the surgical implant. As illustrated, the implant 60 comprises a piton member 62 having an eyelet 64 formed thereon. The piton member 62 preferably comprises an arcuate blade having proximal and distal ends, the latter being designed to be inserted into bone such that as the same is advanced therein, there is defined a penetration pathway as indicated by the letter "A". Once inserted into the bone tissue at the target site of fixation, the eyelet portion 64 of the implant will extend therefrom as illustrated in FIG. 6(a), which will thus provide the necessary structure to which the sutures 66, grafts and the like may be attached. Although the embodiment shown depicts the use of an eyelet 64, it will be recognized that other substitute support or attachment structures, such as posts, hooks and the like, including even swedged-on fixation of the suture or graft to the piton, may be utilized as may be necessary for a given application.

As will be appreciated by those skilled in the art, by inserting the implant in the direction indicated by the letter "A", it will be appreciated that to the extent a force is applied thereto, such as by suture 66 or graft, via a vector having an orientation in the general direction of letter "B", such force will necessarily cause the implant to wedge deeper and become more secure into position within the bone 38, and will thus cause the same to become more rigidly affixed into position, unlike prior art devices which have a tendency to become loose and potentially dislodged with the application of greater amounts of pressure and strain thereto.

Such implant further provides the advantage of being easy to remove. In this regard, due to its orientation within the bone, to the extent a pulling force is applied to the implant in the direction indicated by the letter "C", such implant 60 will be caused to become easily dislodged from its seated position to the extent it becomes necessary to remove and/or reposition such implantable fixation device. Such ease of removal advantageously provides for a simpler, less traumatic procedure than those procedures involving prior art screw and anchor fixation devices.

Referring now to FIGS. 7(a) and 7(b), there is shown a second embodiment 70 of a surgical implant designed to be embedded within bone or soft tissue to which may be attached sutures, grafts and the like. Such embodiment 70, similar to the embodiment 60 depicted in FIG. 6, is specifically designed such that the same becomes more firmly seated into position within the bone to the extent a force is applied in a first direction, as indicated by the letter "D". FIG. 7(a) depicts the surgical implant 70 assuming an insertion configuration which enables the same to be implanted into bone at a target site selected by the surgeon. Such implant is provided with a piton member 72 having opposed flanges 72a, 72b formed at the distal end thereof that are designed to spread apart in the directions Y and Z and become more deeply embedded within the bone to the extent a pressure is applied in a direction indicated by the letter "D". Although the specific embodiment 70 shown depicts that the opposed flanges 72a, 72b flare outwardly, it is to be understood that such flanges can be designed to curve inwardly. Moreover, although such embodiment depicts two opposed flanges, it should be recognized that such implant may have three or more flanges and that each respective flange may be designed to flare outwardly, as shown, or hook inwardly as may be needed to a specific application.

Once firmly embedded within the bone, the eyelet portion 74 of such implant may be utilized to attach sutures and the like. Of additional advantage, similar to the embodiment shown in FIG. 6, is the fact that such implant 70 may further be easily removed to the extent a pulling or opposed force is applied in the direction indicated by the letter "E". As such, to the extent it becomes necessary to remove or otherwise reposition such anchoring device, such anchoring device 70 may be easily dislodged by application of such force. As will be appreciated, such design allows for easier and less traumatic removal than prior art anchor and screw fixation devices.

Referring now to FIG. 8, there is shown a third embodiment 80 of a surgical tissues implant useful as a fixation device to attach sutures, tissues, and grafts to bone, periosteum, and soft tissue. As per the other embodiments, such implant 80 includes a piton member 82, preferably formed as a sickle-shaped member, having an eyelet 84 formed on the proximal end thereof. Such implant 80 is designed to be embedded into the bone or other tissue in the direction indicated by the letter "F". Once so secured into position, forces may be applied thereto, via eyelet 84 in the direction indicated by the letter "G", which will thus work to further embed the piton member 82 into the bone via the penetration pathway defined by the distal end of the piton member 82 so that the implant becomes more secure therewithin. Likewise, to the extent it becomes necessary to remove such device 80, such device may be removed by pulling or otherwise rearwardly retracting the implant in the direction indicated by the letter "H" which, as discussed in the other embodiments, provides for simpler and less traumatic procedure than prior art methodology.

Although each of the aforementioned embodiments 60, 70, 80 are particularly well-suited for insertion into bone, it should be recognized by those skilled in the art that the same may be utilized to affix sutures, grafts, tissues, synthetic materials and the like to connective tissue, and in particular, periosteum as per the further embodiments discussed more fully below. In this respect, each of the aforementioned embodiments 60, 70, 80 may be designed such that the piton portion thereof pierces into and becomes embedded within such tissue and remains firmly seated thereat so that the attachment mechanism formed thereon can provide a service to which the sutures, grafts and the like may be attached.

As will further be appreciated, in each of the embodiments 60, 70, 80 depicted in FIGS. 6–8, the orientation of each of the implants as the same are embedded into the bone or tissue is crucial for the necessary operation thereof. In this regard, it will be appreciated that the implant must be oriented such that the resultant tension or strain applied thereto will cause the piton portion thereof to advance in the penetration pathway defined thereby. Otherwise, to the extent tension is applied in an opposed direction, such implant may be caused to dislodge from its seated position. As a consequence, it will be appreciated that the implants of the present invention must be selectively positioned, and that the surgeon must take great care in making certain that the ultimate tension applied thereto is oriented to facilitate the attachment of the implant to the bone, as opposed to causing the same to become dislodged therefrom.

Referring now to remaining drawings 9–15, and initially to FIG. 9, there are depicted further embodiments of the present invention that are directed to devices for attaching sutures, grafts, tissues and the like to periosteum 36 (i.e., the thick fibrous membrane covering the surface of bones), as well as other types of soft tissue. In this regard, each of the embodiments herein preferably do not penetrate or otherwise become embedded within the bone 38, but rather are attachable to the periosteum 36 at a specific site thereof. However, it should be expressly understood that such embodiments may be modified or otherwise adapted to penetrate and become embedded within the bone 38, as may be necessary or ideal for a given medical procedure.

As will be appreciated by those skilled in the art, a wide variety of surgical procedures requiring fixation of sutures, grafts and the like, such as transvaginal sling surgery, particularly when performed in accordance to the procedure depicted in FIGS. 1 and 2, frequently do not necessitate the use of devices, such as those depicted in FIG. 5, that must necessarily be screwed or anchored within the bone. Quite unexpectedly, it has recently been reported at a meeting sponsored by the American UroGynecologic Society that by utilizing the periosteum 36 as a point of affixation, such affixation can be made more quickly and atraumatically than the utilization of prior art bone screws and anchors, but at the same time achieving satisfactory, if not superior, structural support. In this regard, deployment of such prior art bone-screw/anchor devices is generally considered an excessive measure insofar as such devices are known to provide an excess amount of support than what is typically required or suitable for such particular purpose. However, due to the fact that no feasible alternative had been available until now, such bone screw and anchor devices are utilized, which can substantially complicate such surgical procedures as well as cause the patient to endure unnecessary trauma, possibly delayed recovery time, and possibly higher risk of infection.

In the first of such embodiments depicted in FIGS. 9 and 10, there is provided an affixation device 90 comprised of at least one, and preferably a multiplicity of piton members 92 mounted upon a base member. Each one of the multiplicity of pitons 92, which may take the form of a hook as shown, is designed to ensnare with and become embedded in a target site of soft tissue of the periosteum 36, as depicted in FIG. 9, but not penetrate or otherwise disrupt the outer surface of the bone 38 therebeneath. In this respect, the piton members 92 may be designed such that with light pressure the same only penetrate within a certain limited depth of the periosteum 36 or tissue, such that the same provide a moderate degree of fixation and can be easily removed, or with greater pressure the same penetrate deeper so that the device 90 can become more securely embedded within the periosteum 36 or tissue to thus provide for a more secure base or attachment. Formed on the base member 94 is an attachment means, which may comprise a post or eyelet 96 as shown, to which may be attached the suture 98 or graft. As will be appreciated, the affixation device 90 need only be placed against the periosteum 36 at a target location such that the piton members 92 thereof become embedded therewithin. Because the piton members 92 of the affixation device are caused to only become embedded within the periosteum 36, such novel fixation device may be easily removed and repositioned as may be necessary in a given surgical procedure to insure that an optimal degree of support or positioning is attained.

Once so optimally positioned, the suture 98 or graft may be attached to the device 90 as per conventional surgical procedures. Alternatively, due to the ease by which the affixation device 90 may be detached and reattached, the surgeon is provided with the option of securing the suture 98 or graft to such affixation device 90 and thereafter positioning the affixation device 90 at a target site for best positioning. Advantageously, although the affixation device 90 is specifically designed to provide for easy dislodgment and repositioning, it is believed that once the same is secured into position, due to the eventual overgrowth of tissue about such device 90, the affixation device will continue to provide firmer and stronger support over time.

Figures 11, 12, 13:
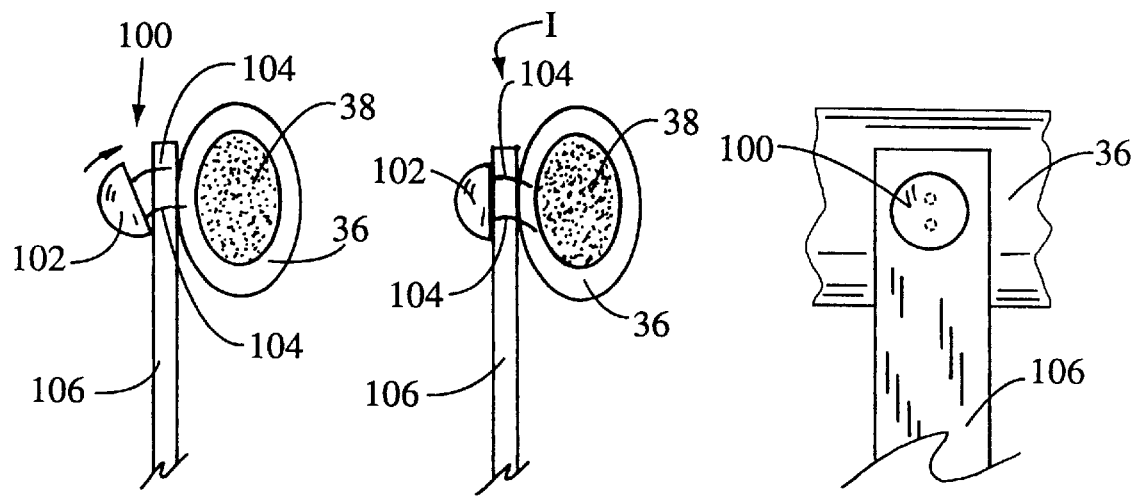
FIG. 11 is a cross-sectional view of the pubic bone and periosteum formed thereabout having an opposed end of a graft being secured thereto with an implantable tack, the latter being constructed in accordance with a fifth preferred embodiment of the present invention.
FIG. 12 is a cross-sectional view of the pubic bone and periosteum formed thereabout showing the graft depicted in FIG. 11 being secured thereto via the implantable tack.
FIG. 13 is frontal view of the graft depicted in FIGS. 11 and 12 as secured to the periosteum via the implantable tack of the present invention.

Referring now to FIGS. 11–13, there is shown a second embodiment 100 of an affixation device useful in the attachment of sutures, grafts, tissues and the like to periosteum, soft tissue, and bone. In the embodiment shown, such affixation device 100 comprises a tack member having a hub portion 102 and at least one, and preferably two or more, prong members 104 formed thereon. As illustrated, the implantable tack 100 may be utilized to affix a graft 106 or other like tissue to the periosteum 36 by merely interposing the graft 106 between the periosteum and the tack 100 and compressing such tack 100 thereagainst such that the prongs 104 thereof extend therethrough and become embedded in the periosteum 36 as systematically shown in FIGS. 11 and 12.

As will be recognized, the prong portions 104 of such tack 100 will be specifically designed and configured to extend through a given layer of tissue or graft material 106 and become embedded into the periosteum 36, but not otherwise extend to or penetrate the bone 38 lying therebeneath (although the embodiment may be modified for such applications). It will further be appreciated that such prongs 104 may vary in number and may take any of a variety of shapes and configurations necessary to achieve that end. As discussed above, it is contemplated that the prong members 104 may be designed to penetrate within the soft tissue, periosteum 36, or even bone 38 at specified depths to thus provide for selective degrees of attachment thereto. In this regard, it is specifically contemplated that such prong members 104 may be formed to have a straight, hook or arcuate shape such that the same facilitate the affixation of a graft 106 to the target site of fixation. For example, in FIG. 12 it will be recognized that due to the arcuate shape of the prong members 104 of the implantable tack 100, when a force is applied in a direction indicated by the letter "I", such force will actually cause the prong members 104 of such implantable tack 100 to penetrate further within the periosteum 36 to thus cause the affixation to become more secure with increased tension. Furthermore, by utilizing a hub member 102 as part of the implantable tack 100, as illustrated in FIG. 13, such implantable tack 100 can be easily accessed and removed in later surgical procedures. To facilitate such removal, a grip, protrusion or an aperture formed upon the hub may be provided. For example, it is contemplated that an attached material, such as a synthetic mesh "extension" or sleeve, may be formed upon the hub 102.

Figures 14, 15:
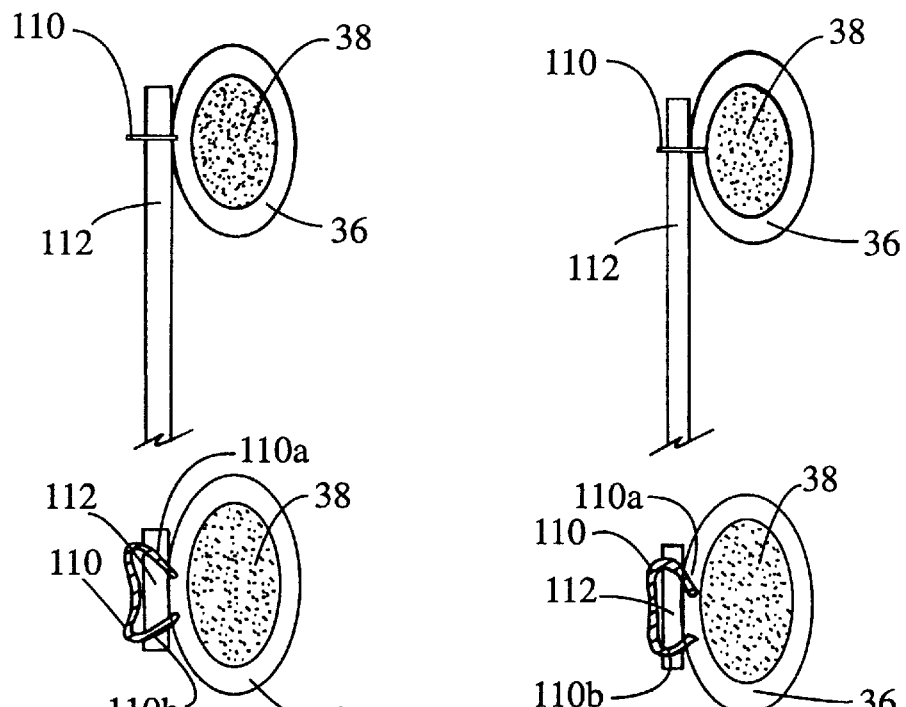
FIG. 14 is a cross-sectional view further depicting an expanded view of the pubic bone with periosteum formed thereabout having an opposed end of the surgical sling affixed to the periosteum via a surgical staple, the latter being constructed in accordance with a sixth preferred embodiment of the present invention, the staple assuming a first insertion mode.
FIG. 15 is a side-view depicting the surgical staple depicted in FIG. 14 securing an opposed end of the sling to the periosteum, the staple assuming a second, affixation configuration.

Referring now to FIGS. 14 and 15, there is shown yet another preferred embodiment 110 of the present invention that comprises a novel surgical staple for securing sutures, tissues or grafts 112, to the periosteum 36. As illustrated, the staple 110 is operative to penetrate through a segment of tissue or graft 112 and become embedded within the periosteum 36 such that the graft or tissue is caused to become affixed therewith. As illustrated in the top view portion of FIG. 14, the staple is operative to assume a first insertion configuration whereby the prongs 110a, 110b of such staple 110 are advanced through the graft 112 and ultimately into the periosteum 36. Thereafter, as illustrated in the top view of FIG. 15, the prongs 110a, 110b are caused to embed within the periosteum 36 to enhance the attachment therewith. As may be necessary for a certain application, such prongs 110a, 110b may even be caused to embed within the bone 38 lying there underneath to thus provide a more secure attachment.

To facilitate the ability of the staple 110 to secure the graft 112 to the periosteum 36 in the aforementioned manner, it is contemplated that such staple 110 may be formed of resilient, self-expanding or self-contracting material which is biased to the operative configuration shown in FIG. 15 such that when unconstrained, the opposed ends of the staple 110 will become further embedded into the periosteum. Similarly, such staple may be fabricated from a plastically deformable material which is initially formed to assume the insertion configuration depicted in FIG. 14, but can subsequently be deformed to assume the operative configuration depicted in FIG. 15. As a still further alternative, such staple 110 may be formed from a shape-memory material, such as nitinol, which thus enables the staple to assume the insertion configuration depicted in FIG. 14 when at room temperature, but transition to the operative, more secure configuration depicted in FIG. 15 when warmed to body temperature, as will occur such staple is deployed. As a further advantage, to the extent it becomes necessary to remove or otherwise reposition such staple 110, it will be recognized by those skilled in the art that removal of such staple 110 may be facilitated by merely cooling the same down by any of a variety of well-known methods, including applying cold saline thereto.

All of the affixation devices discussed herein, although having widespread applicability and substantial advantage over prior art anchor devices, and more particularly bone screws and bone anchors, are particularly well suited in gynecologic and urologic surgical applications. It is believed that such affixation devices are particularly well suited for transvaginal sling surgery insofar as much of the medical literature tends to indicate that in a vast majority of patients, the sling that is utilized in such procedures should be placed with little to no tension at all, with the tension vector emanating therefrom being oriented in a direction well-suited to the piton portion of those embodying as depicted in FIGS. 6–8. Indeed, considerable authority exists that optimal placement of the sling in transvaginal sling surgery occurs when the sling merely comes into contact with the urethra. Affixation by attaching the sling merely to the periosteum and not to the bone is thus believed to provide more than sufficient leverage or support to the sling in such applications, but yet have the further advantage of being exceptionally easy to secure and re-secure into position in a much less traumatic manner than the prior art devices.

Although the invention has been described herein with specific reference to a presently preferred embodiment thereof, it will be appreciated by those skilled in the art that various, modifications, deletions, and alterations may be made to such preferred embodiment without departing from the spirit and scope of the invention. For example, it will be recognized that the piton portion of any of the surgical implants disclosed herein may take any of a variety of forms such that the same are caused to become more thoroughly seated in a position via the application of force in one direction, but yet become more easily withdrawn when pulled rearwardly in a second direction. It is further contemplated that such embodiments may be formed from plastically deformable or shape-memory materials to thus facilitate fixation of such devices at a selected targer site. Moreover, it should be recognized that the affixation devices disclosed herein designed to affix sutures, grafts, tissues, synthetic materials, and the like to periosteum may further be modified so that the same additionally penetrate into and become embedded within the bone lying thereunderneath. Specifically, with respect to the embodiment depicted in FIG. 10, one or more of the hooks may be sized and adapted to penetrate into the bone, similar to the prongs formed on the implantable tack depicted in FIGS. 11–13. Likewise, the prongs of the staple element depicted in FIGS. 14 and 15 may be designed to penetrate and embed within the bone. Accordingly, it is intended that all reasonably foreseeable additions, modifications, deletions and alterations be included within the scope of the invention as defined in the following claims.

What is claimed is:

1. A surgical implant for securing sutures, graphs, synthetic materials, in soft tissue to bone or soft tissue at a selected target site comprising:
   a) a piton member formed from non-bioabsorbable material having proximal and distal ends, said distal end comprising at least two opposed outwardly-flaring prongs for piercing directly through in thereafter becoming embedded within said bone or soft tissue such that each respective one of said prongs defines a dedicated pathway of penetration therewithin:
   b) an attachment member formed upon said proximal end of said piton member, said attachment member being formed from non-bioabsorbable material and designed to receive and securably hold said suture, graph or soft tissue such that a strain is imparted thereto;
   c) wherein said attachment member is formed relative said piton member such that in use, when said suture, graph or soft tissue is attached to said attachment member and tension is applied thereto, such strain is imparted about a first axis and said prongs of said piton member are caused to advance towards said dedicated pathways of penetration; and
   d) wherein said dedicated pathways of penetration and said first axis are not parallel to one another.

2. A surgical implant for securing sutures, graphs, synthetic materials, in soft tissue to bone or soft tissue at a selected target site comprising:
   a) a piton member formed from non-bioabsorbable material having proximal and distal ends, said distal end comprising at least two opposed outwardly-flaring prongs for piercing directly through in thereafter becoming embedded within said bone or soft tissue such that each respective one of said prongs defines a dedicated pathway of penetration therewithin:
   b) an attachment member formed upon said proximal end of said piton member, said attachment member being formed from non-bioabsorbable material and designed to receive and secureably hold said suture, graph or soft tissue such that a strain is imparted thereto;
   c) wherein said attachment member is formed relative said piton member such that in use, when said suture, graph or soft tissue is attached to said attachment member and tension is applied thereto, such strain is imparted about a first axis and said prongs of said piton member are caused to advance towards said dedicated pathways of penetration; and
   d) wherein said dedicated pathways of penetration and said first axis are parallel to one another.

* * * * *